United States Patent [19]

Faber

[11] 4,400,468
[45] Aug. 23, 1983

[54] PROCESS FOR PRODUCING ADIPIC ACID FROM BIOMASS

[75] Inventor: Marcel Faber, Princeton, N.J.

[73] Assignee: Hydrocarbon Research Inc., Lawrenceville, N.J.

[21] Appl. No.: 308,336

[22] Filed: Oct. 5, 1981

[51] Int. Cl.$^3$ .................. C12P 7/44; C12R 1/025; C12R 1/425; C12R 1/645; C12R 1/685; C12R 1/64

[52] U.S. Cl. .................. 435/142; 435/813; 435/823; 435/881; 435/910; 435/911; 435/917; 127/37; 568/863

[58] Field of Search .............. 435/142, 813, 823, 881, 435/910, 917, 911; 127/37; 568/863

[56] References Cited

U.S. PATENT DOCUMENTS

| | | | |
|---|---|---|---|
| 2,271,083 | 1/1942 | Lorand | 568/863 |
| 2,290,439 | 7/1942 | Lenth et al. | 568/863 |
| 2,948,658 | 8/1960 | Green | 435/823 |
| 3,234,105 | 2/1966 | Motizuki et al. | 435/823 |
| 3,651,221 | 3/1972 | Conrad et al. | 435/823 |
| 3,859,369 | 1/1975 | Copelin | 568/863 |
| 4,201,596 | 5/1980 | Church et al. | 127/37 |
| 4,342,831 | 8/1982 | Faber et al. | 127/37 |

FOREIGN PATENT DOCUMENTS 1300455 12/1972 United Kingdom .

OTHER PUBLICATIONS

Kirk–Othmer Encyclopedia of Chemical Technology, vol. 11, 3rd Edition, John Wiley & Sons, New York, 499–514, 523 (1980).

Primary Examiner—Esther M. Kepplinger
Attorney, Agent, or Firm—V. A. Mallare; F. A. Wilson

[57] ABSTRACT

A process is provided for producing adipic acid from a renewable resource, i.e., biomass. The process comprises: hydrolyzing the renewable resource to provide 5-hydroxymethylfurfural, hydrogenating the 5-hydroxymethylfurfural in the presence of a catalyst to provide 2, 5-tetrahydrofurandiomethanol, treating the 2, 5-tetrahydrofurandiomethanol with hydrogen in the presence of a catalyst to provide 1, 6 hexanediol, and oxidizing the 1, 6 hexanediol in the presence of a microorganism to provide adipic acid. The formation of the adipic acid is provided with the microorganism of *Gluconobacter oxydans* subsp. *oxydans*. The renewable resources are wastes selected from the group consisting of paper, wood, corn stalks, and logging residues.

12 Claims, 2 Drawing Figures

PROCESS FOR PRODUCING ADIPIC ACID FROM BIOMASS

BACKGROUND OF INVENTION

This invention relates to a process for producing adipic acid. In particular, this invention relates to a process for producing adipic acid from natural resources such as biomass, including paper and wood.

The processes for producing adipic acid according to industry at the present time are no doubt several in number. A particular process, illustrated below in FIG. 1, shows the production of adipic acid from benzene. In this process, the benzene is heated to form cyclohexane which is oxidized to provide the product, i.e., an industrial product, adipic acid. This process known to many industrial manufacturers, is a useful process except that the cost for producing adipic acid by this means is quite excessive and in many aspects the production of adipic acid by this process is impractical and is generally prohibitive.

In view of the processes provided in the present industry, there is a need for manufacturing adipic acid by less expensive means, i.e., the means provided by the present invention where adipic acid is produced from renewable resources or waste, such as paper, wood, and the like. Thus, the need for such process is fulfilled by the present invention as disclosed and discussed below.

SUMMARY OF INVENTION

The present invention provides a process for producing adipic acid from biomass. The biomass includes materials such as paper, wood, corn stalks and any low cost renewable resources, i.e., waste. The process comprises hydrolyzing the biomass to provide 5-hydroxymethylfurfural, hydrogenating the 5-hydroxymethylfurfural to provide 5-tetrahydrofurandiomethanol, treating the 2, 5-tetrahydrofurandiomethanol with hydrogen in the presence of a catalyst to provide 1, 6 hexanediol, and oxidizing the 1, 6 hexanediol in the presence of a microorganism to provide adipic acid. In the process where 1, 6 hexanediol is converted to adipic acid, the microorganism is *Gluconobacter oxydans* subsp. *suboxydans*.

BRIEF DESCRIPTION OF DRAWINGS

The present invention will be more clearly understood from the detailed description provided below when considered in conjunction with the drawings, wherein.

DETAILED DESCRIPTION OF PREFERRED EMBODIMENT

In the present process for producing adipic acid, in contrast to those of the prior art, the acid is produced from biomass or a renewable resource or waste such as paper, wood, corn stalks, and the like.

Figure 2:
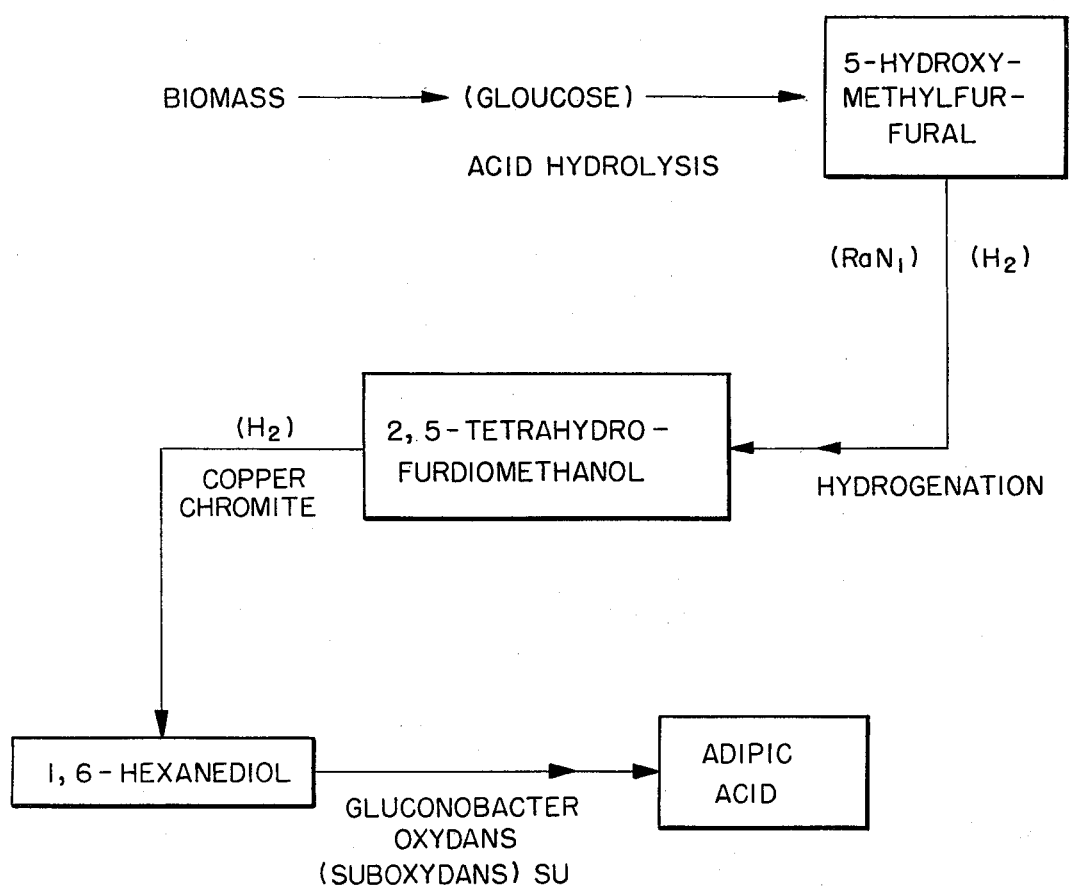
FIG. 2 is a flow diagram of the process for producing adipic acid according to the present invention.

Referring to FIG. 2, the starting material, i.e., biomass, is treated, i.e., hydrolyzed at an elevated temperature with the application of steam to provide 5-hydroxymethylfurfural. The 5-hydroxymethylfurfural is then hydrogenated with an appropriate amount of hydrogen in the presence of a catalyst such as Raney Nickel (RaNi) to provide 2, 5-tetrahydrofurandiomethanol. The 2, 5-tetrahydrofurandiomethanol is then treated with hydrogen in the presence of a catalyst to provide 1, 6 hexanediol. Subsequently, the 1, 6 hexanediol is oxidized in the presence of a microorganism to provide the adipic acid. Overall, the present process in its different steps, is performed in respective vessels of the size that is necessary for carrying out each of such reactions.

Figure 1:
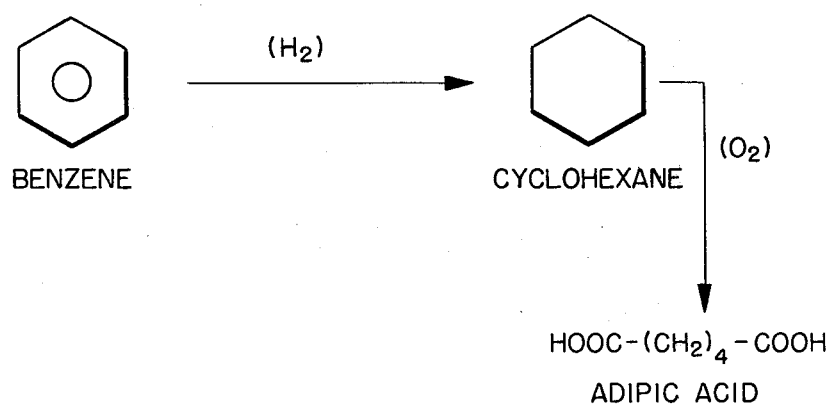
FIG. 1 is a flow diagram of a process used in industry for producing adipic acid.

The present process is an improvement in both efficacy and output for the production of adipic acid from biomass such as paper and/or wood. Referring to FIG. 1, a process generally used and well known in industry to produce adipic acid is illustrated. As shown, in the process benzene is used as a starting material and heated to provide cyclohexane. The cyclohexane is then treated with an oxygen bearing material or oxygen itself to provide the adipic acid. The present process instead of beginning with an expensive starting material, such as benzene, begins with renewable resources, i.e., waste materials such as paper, wood, corn stalks, logging residues and the like.

Referring to FIG. 2, the present process is illustrated by a flow diagram where the biomass is treated in successive steps to provide intermediates which are treated to produce adipic acid.

In the acid hydrolysis of the biomass which is a renewable resource, such as paper, wood, corn stalks, or the like, the biomass is treated in a weak aqueous medium such as a sulfuric or hydrochloric acid. In the dilute acid medium, the cellulose portion of the biomass is broken down into an intermediate sugar compound such as glucose. The glucose in the weak aqueous acid medium is further dehydrated to produce 5-hydroxymethylfurfural (5-HMF). In the acid hydrolysis of the biomass to the sugar intermediate, steam may be added in an amount sufficient to maintain the reaction biomass at a temperature of about 100° to about 250° C. This phase in which the biomass is a sugar is not a stable phase and the period of time that the biomass is glucose or a sugar is short and the material in that form is not isolated or separated. The period of time in which the hydrolysis takes place may be anywhere from about 15 seconds to about 5 hours.

In the hydrogenation of the 5-hydroxymethylfurfural (5-HMF) to provide the 2,5-tetrahydrofurandiomethanol, the 5-HMF is treated with hydrogen in the presence of a catalyst such as Raney Nickel (RaNi). Other catalysts may be used such as a chromium catalyst or the like. The hydrogen is generally fed in a ratio of hydrogen gas to the 5-hydroxymethylfurfural feed, ranging from about 200 to 3000. The hydrogenation may take place in an ebullated bed reactor wherein the 5-HMF is fed downward through the ebullated catalyst (e.g., Rainey Nickel) bed at a temperature ranging from about 100° to about 200° C.

The treatment or the hydrogenolysis of the 2, 5-tetrahydrofurandiomethanol generally takes place in a fixed catalyst bed. The catalyst may be a copper chromite catalyst. The process is carried out at a temperature ranging from about 200° to about 350° C. under a pressure ranging from about 1000 to about 20,000 psi.

In oxidizing the 1, 6 hexanediol to provide the product adipic acid, a microorganism is utilized as a catalyst. A wide variety of microorganisms may be used in the present process. The most suitable microorganisms are of the family *Pseudomonadacae Imperfecti*. Microorganisms which are useful in the practice of this invention include, e.g., *Gluconobacter oxydans* subsp. *oxydans* and other genera of Gluconobacter. In addition, microorganisms such as *Asperguillus niger, Ustulina deusta,* and bacteria such as *Xanthomonas oryzae* and *Serratia marcescens* are known to oxidize an alcohol to a carboxylic acid. The immediate form in which the adipic acid is formed in the liquid phase from which the final product is precipitated and crystallized.

The present process, although related to known processes, is more economical and effective in that from material that would not be used, i.e., a waste, there is provided a means by which a very useful material in industry, i.e., adipic acid, can be produced.

In view of the above discussion of the present invention, it is contended that it would be in the realm of one of ordinary skill in the art to utilize the disclosure herein to develop other means of producing adipic acid. However, this development should not be expected to avoid the present invention as defined in the appended claims.

I claim:

1. A process for producing adipic acid from biomass, a renewable resource, said process comprising:
    (a) hydrolyzing biomass with sufficient steam and dilute acid to provide 5-hydroxymethylfurfural;
    (b) hydrogenating said 5-hydroxymethylfurfural in the presence of a catalyst to provide 2,5-tetrahydrofurandiomethanol;
    (c) treating said 2,5-tetrahydrofurandiomethanol with hydrogen under pressure of at least about 1,000 psi and in the presence of a catalyst at a temperature of from about 200° to about 350° C. to provide 1, 6 hexanediol; and
    (d) oxydizing said 1, 6 hexanediol in the presence of a microorganism to provide adipic acid.

2. The process according to claim 1, wherein said biomass resource is a waste material selected from the group consisting of paper, wood, corn stalks and logging residues.

3. The process according to claim 1, wherein the hydrolysis of said biomass is carried out at a temperature ranging from about 100° to about 250° C.

4. The process according to claim 1, wherein said hydrolysis of said biomass, said steam is provided in an amount sufficient to maintain said biomass at a temperature of about 100° to about 250° C.

5. The process according to claim 1, wherein the 2,5-tetrahydrofurandiomethanol is treated with hydrogen under a pressure ranging from about 1,000 to about 20,000 psi.

6. The process of claim 1, wherein said 5-hydroxymethylfurfural is hydrogenated in an ebullated catalyst bed at a temperature ranging from about 100° to about 200° C.

7. The method according to claim 1, wherein said hydrogenation of 5-hydroxymethylfurfural, the ratio of hydrogen gas to said furfural ranges from about 200 to about 3,000.

8. The process according to claim 1, wherein said 5-tetrahydrofurandiomethanol is treated with hydrogen in the presence of a copper chromite catalyst at a temperature ranging from about 200° to about 350° C.

9. The process according to claim 1, wherein the microorganism used to oxydize said 1, 6 hexanediol is *Gluconobacter oxydans* subsp. *oxydans*.

10. The process according to claim 1, wherein the microorganism used to oxidize said 1, 6 hexanediol is *Aspergillus niger, Ustulina deusta, Xanthomonas oryzae* or *Serratia marcescens*.

11. The process of claim 1, wherein said hydrolysis of said biomass takes place in period of time of about 15 seconds to about 5 hours.

12. The process of claim 1, wherein said hydrogenation of 5-hydroxymethylfurfural is carried out in the presence of the catalyst Raney Nickel.

* * * * *